(12) United States Patent
Alvarez

(10) Patent No.: US 8,273,090 B2
(45) Date of Patent: Sep. 25, 2012

(54) TIBIAL PLATEAU AND/OR FEMORAL CONDYLE RESECTION SYSTEM FOR PROSTHESIS IMPLANTATION

(75) Inventor: Luis Marquez Alvarez, Reus (ES)

(73) Assignee: Traiber, S.L., Reus (Tarragona) (ES)

( * ) Notice: Subject to any disclaimer, the term of this patent is extended or adjusted under 35 U.S.C. 154(b) by 820 days.

(21) Appl. No.: 12/044,125

(22) Filed: Mar. 7, 2008

(65) Prior Publication Data
US 2009/0228016 A1    Sep. 10, 2009

(51) Int. Cl.
*A61B 17/58* (2006.01)
(52) U.S. Cl. .................... 606/88; 606/86 R
(58) Field of Classification Search .......... 606/86 R, 606/87, 88, 96–98
See application file for complete search history.

(56) References Cited

U.S. PATENT DOCUMENTS

| | | | | |
|---|---|---|---|---|
| 4,901,711 A * | 2/1990 | Goble et al. | | 606/98 |
| 2002/0107522 A1 * | 8/2002 | Picard et al. | | 606/88 |
| 2002/0198531 A1 * | 12/2002 | Millard et al. | | 606/87 |
| 2004/0122436 A1 * | 6/2004 | Grimm | | 606/87 |
| 2005/0119639 A1 * | 6/2005 | McCombs et al. | | 606/1 |
| 2005/0149041 A1 * | 7/2005 | McGinley et al. | | 606/88 |
| 2005/0238418 A1 * | 10/2005 | Surma et al. | | 403/24 |
| 2006/0217733 A1 * | 9/2006 | Plassky et al. | | 606/87 |
| 2007/0118139 A1 * | 5/2007 | Cuellar et al. | | 606/87 |
| 2007/0173850 A1 * | 7/2007 | Rangaiah et al. | | 606/87 |
| 2008/0140081 A1 * | 6/2008 | Heavener et al. | | 606/87 |

* cited by examiner

Primary Examiner — Thomas Barrett
Assistant Examiner — Melissa A Golob
(74) Attorney, Agent, or Firm — Katten Muchin Rosenman LLP

(57) ABSTRACT

According to the invention, the system enables a preoperative study to be carried out wherein the tibia and/or femur is modelled on a computer (6) in 3D, the ideal cutting plane is defined and the position of the resection instruments (1, 2, 3) used to cut the bone is modelled. Additionally, according to the invention, the system enables redefinition of the ideal cutting plane and the positioning and orientation of the resection instruments (1, 2, 3) on the tibia and/or femur, in such a manner that the plane of the slot (4) of the cutting guide (3) through which the cutting tool is introduced coincides with the ideal cutting plane.

9 Claims, 5 Drawing Sheets ized display systems based on a pair of infrared stereoscopic cameras. Once the cameras have been calibrated, it is possible to determine, by means of triangulation, the 3D coordinates of a visible point by both cameras at the same time.

TIBIAL PLATEAU AND/OR FEMORAL CONDYLE RESECTION SYSTEM FOR PROSTHESIS IMPLANTATION

OBJECT OF THE INVENTION

The present invention relates to the field of knee prostheses and, more specifically, proposes a tibial plateau and/or femoral condyle resection method and system for prosthesis implantation.

The object of the invention consists of a system by means of which a preoperative study is carried out to create a 3D model of the patient's tibia and femur for the purpose of defining the ideal cutting plane and modelling the position of the instruments for bone cutting, based on which, during the surgery phase, the data relative to the real position and orientation of the instruments for resectioning along said cutting plane is redefined and transferred to the patient's tibia and femur.

Another object of the invention is the method used to model the tibia and/or femur and determine the cutting or resectioning plane in a preoperative study, in addition to the subsequent surgery phase to adjust the orientation of the cutting instruments in accordance with the determined cutting plane.

Another object of the invention relates to the programme that executes the previously described modelling method.

BACKGROUND OF THE INVENTION

Total knee substitution surgery consists of prosthesis implantation to carry out the function thereof.

The intervention consists firstly of cutting the lower end of the femur and upper end of the tibia, in order to leave a surface whereon to implant the prosthesis elements. Next, a polyethylene insert that allows rotation and compensation of the cut tibia is positioned between these two elements.

A critical success factor in these interventions, for example in relation to the useful life of the prosthesis, is the correct positioning of the prosthesis with respect to the patient's anatomy. In order to correctly perform this implant, a preoperative study is carried out based on a couple of knee X-rays showing two perpendicular (front and side) views. After taking note of the position and/or the angles between certain anatomic characteristics, the surgeon can make calculations to determine the desired position and spatial orientation of the prosthesis (in three dimensions or, rather, two dimensions, one for each view).

Spatial orientation refers to the orientation of the tibial and/or femoral cutting plane. In fact, the surgeon must resect the tibia and/or femur along a plane with a spatial orientation defined by two angles with respect to an imaginary axis that crosses the mechanical axis thereof.

This imaginary axis is mentally created by the surgeon based on direct visual information or fluoroscopic X-ray images. Given that it is a qualitative estimate, sometimes the prosthesis cannot be positioned in the desired alignment.

Therefore, the difficulty of this process lies in transferring the orientation of the cutting plane with respect to the mechanical axis of the bone, determined based on the preoperative images, to the "patient's coordinates" during the surgical intervention with the greatest possible precision.

The solutions applied during the intervention include surgery, use of navigators or robotized systems.

Surgery requires the use of intra or extramedullary guides during the intervention, whereto instruments are coupled to cut the bone in the desired 3D orientation. In relation to this orientation, the surgeon, using the adequate instruments, can operate following a cutting plane. However, if the guide is deviated, this will affect the orientation of the cut and therefore of one part of the prosthesis.

Another solution envisages the use of commercial navigators that consist of computerized display systems based on a pair of infrared stereoscopic cameras. Once the cameras have been calibrated, it is possible to determine, by means of triangulation, the 3D coordinates of a visible point by both cameras at the same time.

Navigation allows the surgeon to create an individual anatomic map for each patient. Prior to the intervention, markers are fixed to the patient's bone (tibia and/or femur). Next, infrared light-emitting diodes (LEDs) are fixed so that these are visible to the cameras. In this manner, the computer can calculate the 3D coordinates (patient) of the markers based on the 2D coordinates of the diodes captured by each camera.

As the emitting diodes are fixed to the patient, it does not matter if the leg moves, due to the fact that its position is constantly recalculated. In this manner, movements and reference points can be recorded and, based on this information, the navigation system shows the position of the instruments in relation to the available patient data on the computer screen. This helps the surgeon to align the instruments during the intervention in such a manner as to ensure correct prosthesis implantation.

Although the use of navigators probably represents the best solution from a technical point of view, on one hand, their economic cost makes them barely accessible for small and medium-sized hospitals and, on the other, the calibration process is slow and must be carried out by the surgeon him/herself, consequently lengthening the duration of the interventions.

Another solution consists of using robotized arms, operated by the computer, which are capable of automatically resecting the bone with the help of a navigator and/or preoperative images. Therefore, these systems are even more complex than navigators.

DESCRIPTION OF THE INVENTION

The method proposed in this invention consists of resecting the tibial plateau and/or femoral condyles along a cutting plane considered ideal by the doctor in the preoperative study, in such a manner as to minimize the possibilities of error and of damaging the tibia and/or femoral condyles when making the cuts.

The preoperative study is aimed at obtaining all the tibia and/or femur geometry data through exploration means that may consist of devices designed to perform scanning, magnetic resonance imaging, X-ray or computerized tomography operations, for example.

These data are processed with the help of a computer, in accordance with a programme developed for such purpose, to reconstruct the tibia and/or femur by generating a virtual 3D model.

Additionally, a virtual reproduction of the instruments used to resect the bone is placed over these images, with measurements and shapes that coincide with those shown by the physical objects.

In general, the resection instruments include a support that is nailed to the bone, a guide holder that is mounted on a support disposed at the end of the positioning support of the cutting guide, and a cutting guide.

The assembly, comprised of a virtual support, virtual guide holder and virtual cutting guide, is attached to this first virtual model of the tibia and femur, establishing the position and orientation of the virtual support on the bone, in such a manner that the plane of the cutting guide slot coincides with the ideal cutting plane selected by the surgeon.

The previously described phases are executed in the preoperative study, after which, during the surgery phase, the support is nailed to the patient's tibia or femur at a point and position that approximately coincide with those obtained for the virtual support.

In order to determine the exact position in which the support has been nailed to the tibia or femur, a reference plate that refers to an X-ray and radio-opaque elements, preferably made of translucent material, is mounted on said support. Subsequently, exploration means are applied to said reference plate, preferably consisting of approximately orthogonal fluoroscopies, which are uploaded to the programme, thereby obtaining a second virtual model that shows the upper profile of the tibia or femur, the support and the reference plate.

In this manner, we can compare the position and orientation of the virtual model with the position and orientation of the real model, as a result of which the computer provides error correction data.

The guide holder's position with respect to the part of the guide holder whereto the support is fixed is adjusted by means of the calibration tool.

Once the guide holder's configuration has been adjusted, it is positioned on the support and the cutting guide positioned within the guide holder, subsequently introducing the cutting tool through the slot in order to resect the bone.

In summary and according to one of the objects of the invention, we also propose a method for modelling the tibia or femur and positional configuration of the resection instruments, which consists of the following phases:
  tibia or femur image capture and generation of a first virtual 3D model of the tibia in order to select the ideal cutting plane of the tibial plateau and/or femoral condyles;
  determination of the position of the cutting instruments according to the ideal cutting plane, based on the virtual model of the tibia and/or femur;
  tibia and/or femur image capture and generation of a second virtual model; and
  determination of the differences between the first virtual model and second virtual model, and presentation of error correction data for the positional configuration of the cutting instruments.

As opposed to other systems, determination of the cutting plane and execution of the cut or resection is carried out in accordance with this method aimed at modelling a patient's tibia and/or femur and which does not require the use of intra or extramedullary guides.

DESCRIPTION OF THE DRAWINGS

For the purpose of complementing the preceding description and to further explain the characteristics of the invention, a set of drawings in accordance with a preferred embodiment thereof has been included as an integral part of said description, in which the following figures have been represented in an illustrative and unlimitative manner, making reference to tibial plateau resection, although it could be equally applicable to femoral condyle resection.

PREFERRED EMBODIMENT OF THE INVENTION

Figure 1:
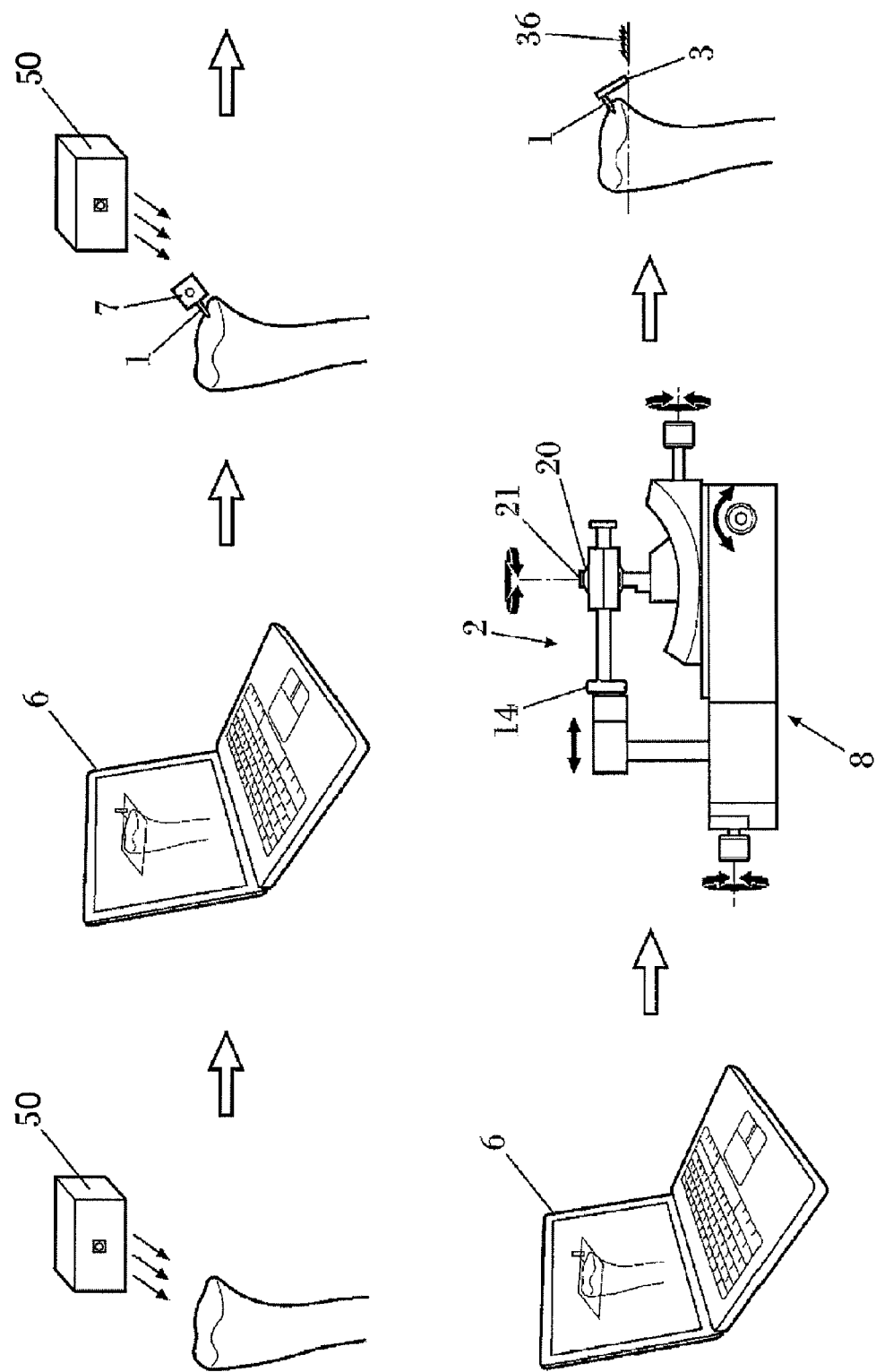
FIG. 1 shows a schematic view of the tibial plateau resection system along a longitudinal axis.

Based on the preceding figures, a description of a preferred embodiment of the tibial plateau resection system is provided below.

The tibial plateau resection system proposed by this invention is based on the fundamental inclusion of:
  A software programme that models the tibia and cutting plane, and calculates the configuration parameters to adapt the cutting instruments (1, 2, 3) and perform the defined cut. The software is comprised of two differentiated parts, a preoperative study programme that models the patient's tibia wherein the surgeon defines, in accordance with the physical characteristics of the tibia, the ideal cutting plane, and a surgery programme that calculates the tool configuration parameters required to perform the cut defined in the preoperative study.
  Cutting or resection instruments (1, 2, 3) comprised of a fixing support (1) represented in FIG. 2, that is nailed to the tibia, a guide holder (2) represented in FIGS. 5 and 6, which is mounted on the fixing support (1) and a cutting guide (3) shown in FIGS. 8 and 9, which has a slot (4) for passage of the cutting tool (36), such as a saw, chisel, blade . . . with which to perform the resection, which at the same time is mounted on the guide holder (2).

As shown in FIG. 1, the system additionally comprises the following elements:
  exploration means (50) for tibia image capture;
  a computer (6) whereto said images are sent and based on which the software models the tibia in 3D and also defines the virtual position of the resection instruments with respect to the tibia along a cutting or resection plane;
  a removable reference plate (7) that is mounted on the fixing support (1) to send, by means of the exploration means (50), images of the position and orientation of the fixing support (1) to the computer (6), where these are compared to the virtual position of the instruments in order to redefine the cutting plane and, consequently, the relative position of the cutting instruments (1, 2, 3); and
  a calibration tool (8) wherein the configuration of the guide holder (2) is adjusted according to the data provided by the program.

Once the configuration of the guide holder (2) is adjusted within the calibration tool, it is mounted on the fixed support (1) which has been previously nailed to the tibia, and the cutting guide (3) mounted on the guide holder (2), subsequently resecting the tibia using the cutting tool (36) that penetrates through the cutting guide (3).

Figure 2:
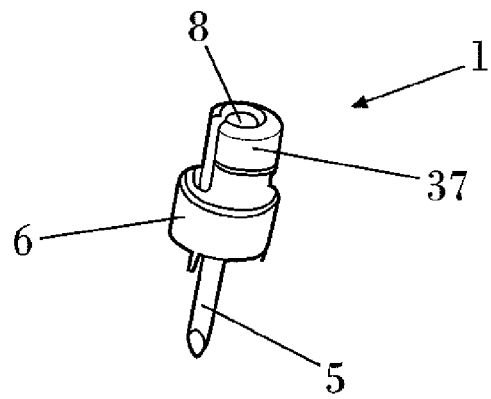
FIG. 2 shows a perspective view of the support.

As shown in FIG. 2, the fixing support (1) comprises a nail (5), a cylindrical central section (6) and a quasi-cylindrical upper section (37) that ends in a vertical plane with a longitudinal bore (8) along its interior.

Figure 3:
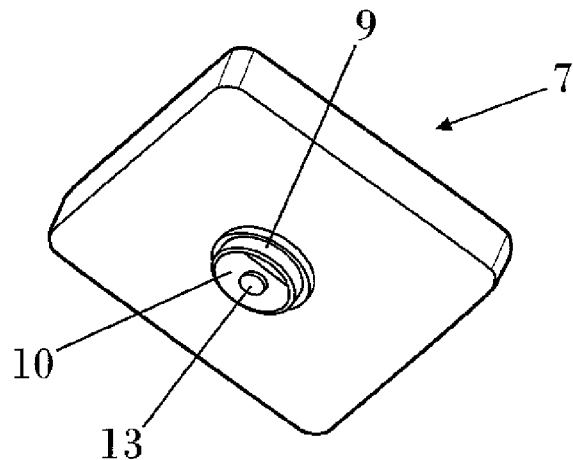
FIG. 3 shows a perspective view from below of the reference plate.
Figure 4:
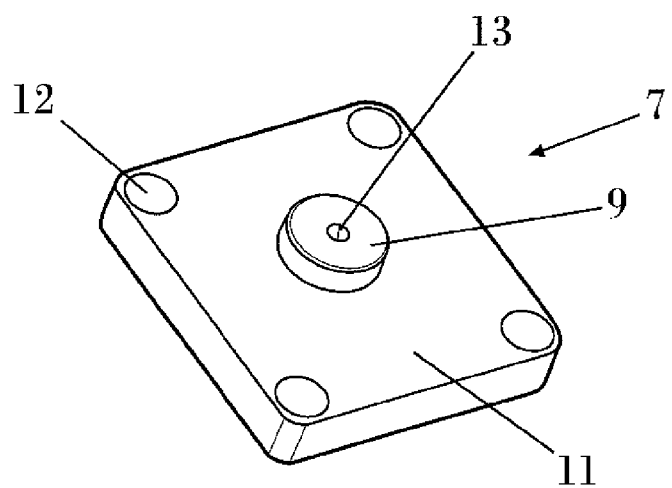
FIG. 4 shows a perspective view from above of the reference plate.

On the other hand, the reference plate (7), as shown in FIGS. 3 and 4, consists of a central body (9) with a cavity (10), the configuration of which is adaptable to the upper section

(37) of the fixing support (1), an X-ray transparent body (11) that surrounds the central body (9) and radio-opaque spheres (12) integrated within said X-ray transparent body (11). A screw (13) threaded into the longitudinal bore (8) of the fixing support (1) can penetrate the cavity (10), thereby joining the reference plate (7) with said fixing support (1).

Figure 5:
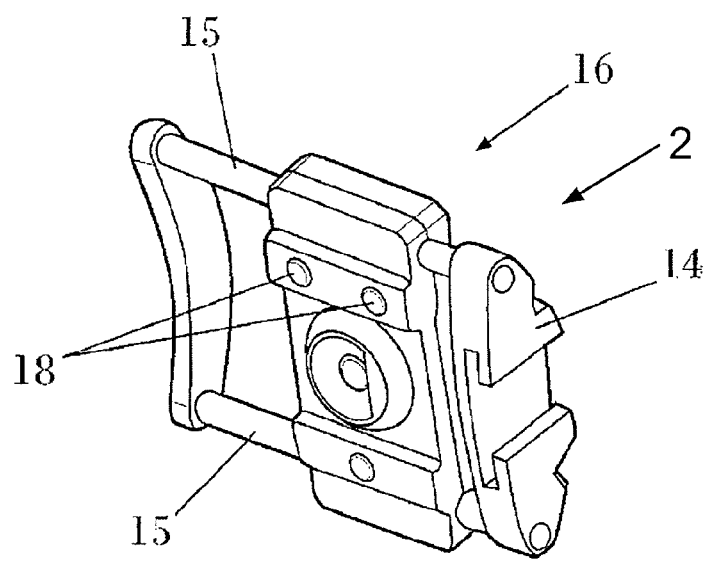
FIG. 5 shows a perspective view from below of the guide holder.
Figure 6:
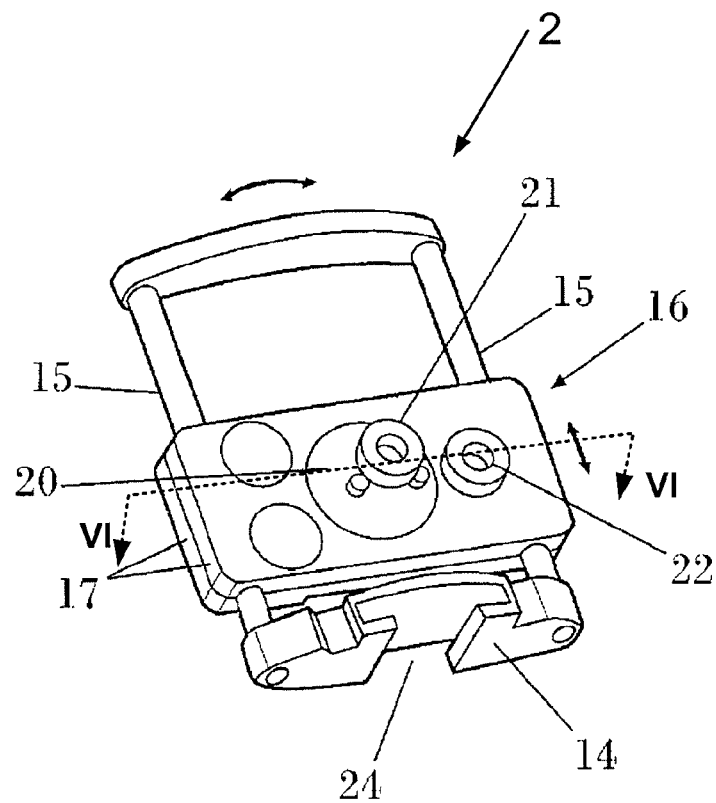
FIG. 6 shows a perspective view from above of the guide holder.
Figure 7:
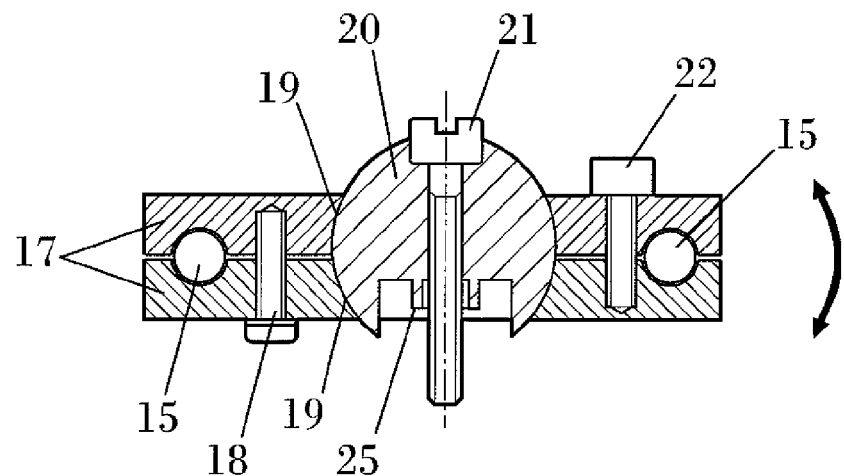
FIG. 7 shows a view of the guide holder along section line A-A represented in FIG. 6.
Figure 8:
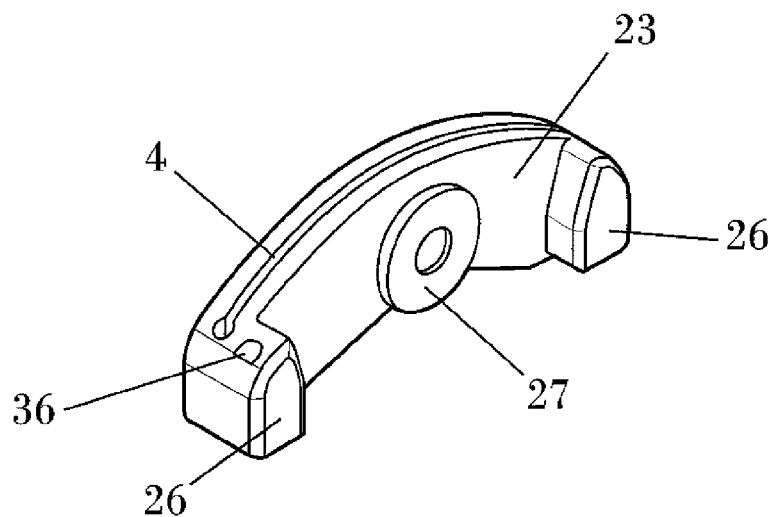
FIG. 8 shows a front perspective view of the cutting guide.

FIGS. 5 and 6 show that the guide holder (2) includes a positioning support for the cutting guide (14), wherein a groove (24) is defined for the purpose of receiving the cutting guide (3), represented in FIG. 8. The positioning support of the cutting guide (14) is solidly joined to parallel shafts (15) joined in turn by their opposing ends, whereon a carriage (16) comprised of two plates (17), upper and lower, joined together by means of screws (18), which slide with respect to the shafts (15) and have corresponding central openings (19), as shown in FIGS. 6 and 7, in which a ball-and-socket joint (20) is disposed, with respect to which the carriage (16) rotates along a horizontal plane and vertical plane. A central screw (21) that joins the guide holder (2) to the fixing support (1) is disposed on this ball-and-socket joint (20), said ball-and-socket joint (20) also having a socket housing (25), the configuration of which can be coupled to the upper section (7) of the fixing support (1).

Figure 10:
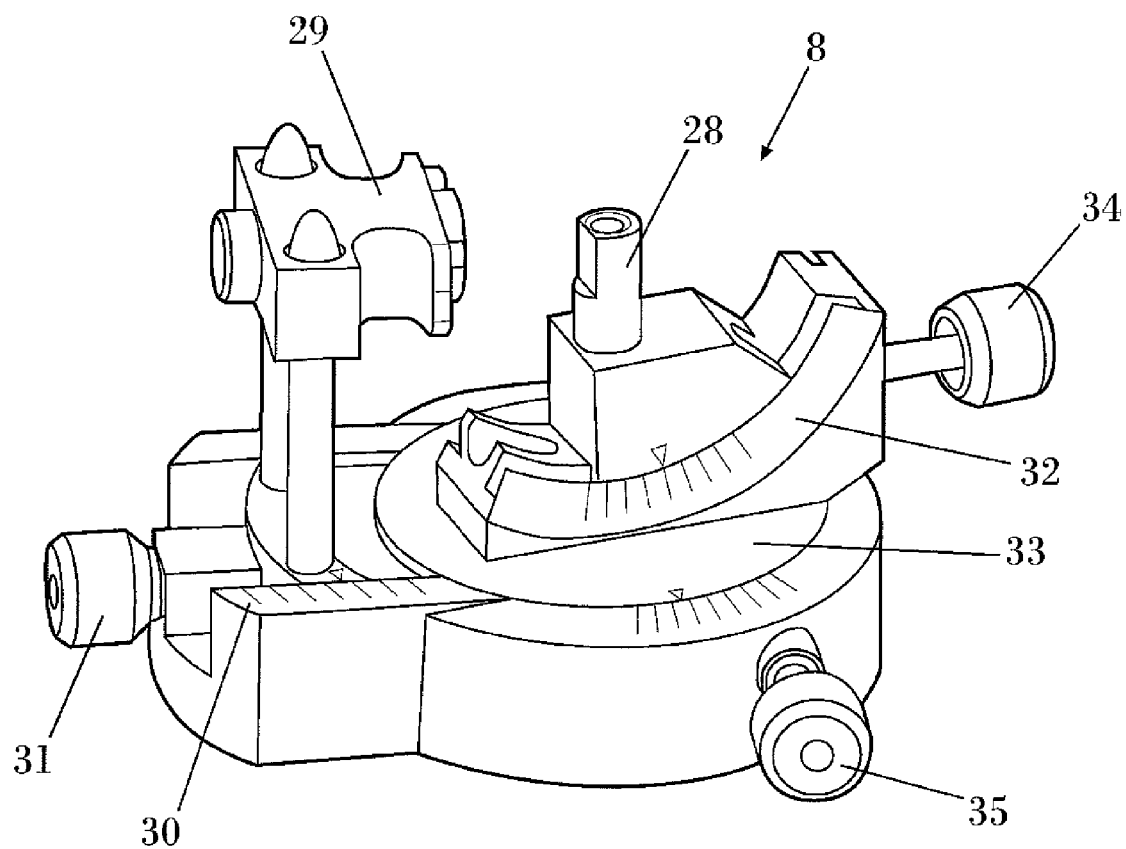
FIG. 10 shows a perspective view of the calibration tool.

According to the preceding explanation, the relative position of the cutting guide (3), or rather that of the guide holder (2) at the end of which the positioning support of the cutting guide (14) that houses the cutting guide (3) is disposed, with respect to the fixing support (1), shall be adjusted by means of the calibration tool (8) represented in FIG. 10. Said calibration tool (8) regulates the distance between the positioning support of the cutting guide (14) and centre of the ball-and-socket joint (20) by displacing the assembly formed by said positioning support of the cutting guide (14) and shafts (15) with respect to the carriage (16). On the other hand, the assembly formed by the positioning support of the cutting guide (14), carriage (16) and shafts (15) can rotate with respect to the ball-and-socket joint (20) by means of a fixing screw (22), as shown in FIGS. 6 and 7, that holds the plates (17) against the ball-and-socket joint (20) and against one of the shafts (15), thereby joining all of the elements that comprise the guide holder (2). In this position, the cutting guide (3), which is mounted on the positioning support of the cutting guide (14) of the guide holder (2), is oriented in such a manner that the slot (4) plane thereof coincides with the ideal cutting plane.

Figure 9:
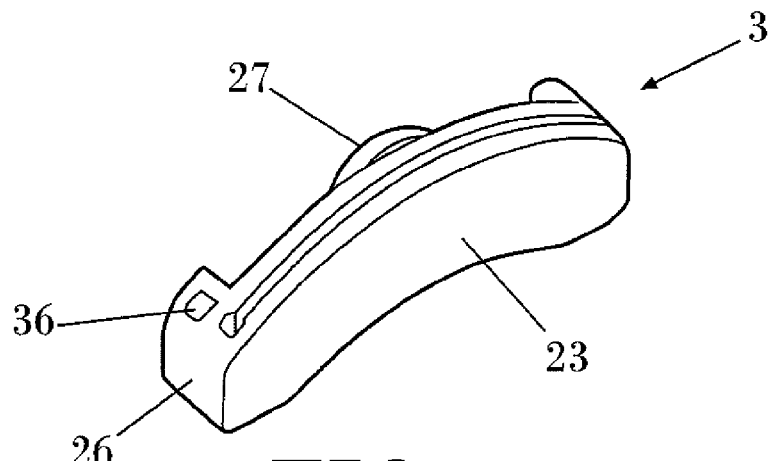
FIG. 9 shows a rear perspective view of the cutting guide.

The cutting guide (3), represented in FIGS. 8 and 9, consists of a flat body (23) wherein the aforementioned slot (4) is defined, having lateral stops (26) disposed at either end, and a circular protuberance (27) disposed on one of the sides of said flat body (23) that fits into the groove (24) of the positioning support of the cutting guide (14) during assembly of the cutting guide (3) on the guide holder (2). Once the cutting guide (3) is positioned, it is fixed to the tibia by means of pins that are introduced through the bores (36).

As shown in FIG. 10, the calibration tool (8) fundamentally includes a coupling shaft (28) having the same shape and size as the upper section (7) of the fixing support (1), whereto the ball-and-socket joint (20) of the guide holder (2) and a support (29) disposed at a distance from the coupling shaft (28), onto which the positioning support of the cutting guide (14) is fitted, are coupled.

This support (29) is mounted on a first block (30) that moves linearly with respect to the coupling shaft (28), with the object of adjusting the distance between the positioning support of the cutting guide (14) and the ball-and-socket joint (20), as shown in FIG. 1, said operation being carried out by means of a first control knob (31).

On the other hand, the coupling shaft (28) of the calibration tool (8) is joined to a second block (32) that rotates along the vertical plane with respect to a third block (33) in order to adjust the relative tilt, along this vertical plane of the positioning support of the cutting guide (14), with respect to the ball-and-socket joint (20), said operation being carried out by means of a second control knob (34).

The third block (33) rotates along the horizontal plane in order to adjust the angular position of the positioning support of the cutting guide (14) with respect to the ball-and-socket joint (20), said operation being carried out by means of a third control knob (35).

The invention claimed is:

1. A resection system for prosthesis implantation in a tibial plateau or a femoral condyle, the resection system comprising:
   a plurality of resection instruments, the plurality of resection instruments comprising
      a fixing support for nailing to a tibia or a femur,
      a guide holder mounted on the fixing support,
      a cutting tool and a cutting guide comprising a slot for passage of the cutting tool, the cutting tool for resecting the tibial plateau or the femoral condyle, the cutting tool being mounted on the guide holder;
   an exploration means for capturing a first image of the tibia or the femur;
   a computer for receiving the first image, modeling the tibia or femur in three-dimensions, and defining a virtual position of the plurality of resection instruments along a cutting plane;
   a removable reference plate mounted on the fixing support to send by means of the exploration means, a second image of a position and orientation of the fixing support to the computer to redefine the cutting plane and position of the plurality of resection instruments; and
   a calibration tool for adjusting the cutting tool;
   wherein the guide holder comprises
      a positioning support for the cutting guide, the positioning support comprising a groove, the cutting guide being received in the grove,
      a pair of parallel shafts solidly joined to the positioning support, each of the pair of parallel shafts comprising a first end and a second ends, the pair of shafts being joined at the first end and the second end,
      a carriage slideably mounted on the pair of shafts, the carriage comprising an upper plate and a lower plate, the upper and lower plate each comprising a central opening, the upper and lower plates joined to each other by a plurality of fastening screws,
      a ball-and-socket joint disposed between the central openings of the plates, the ball-and-socket joint rotating along a horizontal plane and a vertical plane with respect to a plane in which the carriage slides,
      a central screw joining the guide holder to the fixing support, the central screw limiting movement of the ball-and-socket joint,
      a socket housing underneath the ball-and-socket joint, the socket housing being coupled to an upper section of the fixing support, and
      a fixing screw for holding the upper plate and lower plate against the ball-and-socket joint and against one of the shafts to fix a relative orientation of the guide holder with respect to the central screw.

2. The resection system of claim 1, wherein the fixing support comprises a nail, a cylindrical central section, and a substantially-cylindrical upper section that ends in a vertical plane, the fixing support having a longitudinal bore along an interior of the fixing support.

3. The resection system of claim 1, wherein the reference plate comprises
- a central body having a cavity, the cavity having an adaptable configuration to an upper section of the fixing support;
- an X-ray transparent body that surrounds the central body;
- a radio-opaque sphere integrated within the X-ray transparent body; and
- a screw for penetrating the cavity for the central body, the screw being threaded into the longitudinal bore of the fixing support for joining the reference plate with said fixing support.

4. The resection system of claim 1, wherein the exploration means comprises one of scanning, magnetic resonance imaging, X-ray and computerized tomography operations, or image capturing.

5. A resection system for prosthesis implantation in a tibial plateau or a femoral condyle, the resection system comprising:
- a plurality of resection instruments, the plurality of resection instruments comprising
  - a fixing support for nailing to a tibia or a femur,
  - a guide holder mounted on the fixing support,
  - a cutting tool and a cutting guide comprising a slot for passage of the cutting tool, the cutting tool for resecting the tibial plateau or a femoral condyle, the cutting tool being mounted on the guide holder
- an exploration means for capturing a first image of the tibia or femur;
- a computer for receiving the first image, modeling the tibia or femur in three-dimensions, and defining a virtual position of the plurality of resection instruments along a cutting plane;
- a removable reference plate mounted on the fixing support to send by means of the exploration means, a second image of a position and orientation of the fixing support to the computer to redefine the cutting plane and position of the plurality of resection instruments; and
- a calibration tool for adjusting the cutting tool;
- wherein the calibration tool comprises
  - a first control knob, a second control knob, and a third control knob,
  - a coupling shaft having a shape and a size matching an upper section of the fixing support, whereto a ball-and-socket joint of the guide holder is coupled,
  - a support disposed at a distance from the coupling shaft, a positioning support of the cutting guide being fitted to the support,
  - a first block wherein the support is mounted, the support being actuated by the first control knob for enabling a linear displacement with respect to the coupling shaft and adjusting a distance between the positioning support of the cutting guide and the ball-and-socket joint,
  - a second block joined to the coupling shaft of the calibration tool, the second block being actuated by a second control knob for enabling a first rotation of the second block along a vertical plane in order to adjust a relative tilt of the positioning support of the cutting guide with respect to the ball-and-socket joint, and
  - a third block rotatable with respect to the second block, the third block being actuated by a third control knob for enabling a second rotation along a horizontal plane to adjust an angular position of the positioning support of the cutting guide with respect to the ball-and-socket joint.

6. The resection system of claim 5, wherein the carriage is slideable on a pair of parallel shafts.

7. The resection system of claim 5, wherein the fixing support comprises a nail, a cylindrical central section, and a substantially-cylindrical upper section that ends in a vertical plane, the fixing support having a longitudinal bore along an interior of the fixing support.

8. The resection system of claim 5, wherein the reference plate comprises
- a central body having a cavity, the cavity having an adaptable configuration to an upper section of the fixing support;
- an X-ray transparent body that surrounds the central body;
- a radio-opaque sphere integrated within the X-ray transparent body; and
- a screw for penetrating the cavity for the central body, the screw being threaded into the longitudinal bore of the fixing support for joining the reference plate with said fixing support.

9. The resection system of claim 5, wherein the exploration means comprises one of scanning, magnetic resonance imaging, X-ray and computerized tomography operations, or image capturing.

* * * * *